United States Patent
Feng et al.

(10) Patent No.: US 12,377,039 B2
(45) Date of Patent: *Aug. 5, 2025

(54) CLEANSING COMPOSITIONS

(71) Applicant: L'OREAL, Paris (FR)

(72) Inventors: Jianxin Feng, Clark, NJ (US); Heather Yoonsoo Lee, Hoboken, NJ (US)

(73) Assignee: L'OREAL, Paris (FR)

( * ) Notice: Subject to any disclaimer, the term of this patent is extended or adjusted under 35 U.S.C. 154(b) by 673 days.

This patent is subject to a terminal disclaimer.

(21) Appl. No.: 17/587,469

(22) Filed: Jan. 28, 2022

(65) Prior Publication Data

US 2022/0241179 A1  Aug. 4, 2022

Related U.S. Application Data

(60) Provisional application No. 63/143,278, filed on Jan. 29, 2021.

(30) Foreign Application Priority Data

Jul. 21, 2021   (FR) ...................... 2107844

(51) Int. Cl.
*C11D 1/02*   (2006.01)
*A61K 8/34*   (2006.01)
(Continued)

(52) U.S. Cl.
CPC .............. *A61K 8/86* (2013.01); *A61K 8/345* (2013.01); *A61K 8/42* (2013.01); *A61K 8/442* (2013.01);
(Continued)

(58) Field of Classification Search
CPC .. C11D 1/02; C11D 1/662; C11D 1/72; C11D 1/83; C11D 1/90; C11D 3/22;
(Continued)

(56) References Cited

U.S. PATENT DOCUMENTS

| 9,018,150 | B1 | 4/2015 | Rizk |
| 9,271,908 | B2 | 3/2016 | Allef et al. |

(Continued)

FOREIGN PATENT DOCUMENTS

| CA | 2143558 A1 | 8/1996 |
| CA | 2273340 A1 | 6/1998 |

(Continued)

OTHER PUBLICATIONS

International Search Report and Written Opinion issued on Apr. 13, 2022 for corresponding PCT Application No. PCT/US2022/014254.

(Continued)

*Primary Examiner* — Brian P Mruk
(74) *Attorney, Agent, or Firm* — POLSINELLI PC

(57) ABSTRACT

Shampoo composition including about 6 wt. % or more of one or more betaine surfactants; about 5 wt. % or less of one or more anionic surfactants; about 0.1 wt. % to about 10 wt. % of one or more fatty amine surfactants; about 0.1 to about 15 wt. % of one or more nonionic surfactants, wherein at least one of the one or more nonionic surfactants is selected from alkoxylated fatty alcohols, polyethylene glycol ethers of fatty alcohols, or a mixture thereof; and water, wherein all weight percentages are based on the total weight of the shampoo composition. The shampoo compositions typically have a weight ratio of the total amount of the one or more betaine surfactants to the total amount of the one or more anionic surfactants, the one or more fatty amine surfactants, and the one or more nonionic surfactants that is 0.8:1 to 5:1 and are typically substantially free of anionic sulfate surfactants and silicones.

20 Claims, 2 Drawing Sheets

(51) Int. Cl.
*A61K 8/41* (2006.01)
*A61K 8/42* (2006.01)
*A61K 8/44* (2006.01)
*A61K 8/46* (2006.01)
*A61K 8/60* (2006.01)
*A61K 8/86* (2006.01)
*A61Q 5/02* (2006.01)
*C11D 1/72* (2006.01)
*C11D 1/83* (2006.01)
*C11D 3/22* (2006.01)
*C11D 3/30* (2006.01)

(52) U.S. Cl.
CPC .............. *A61K 8/466* (2013.01); *A61K 8/602* (2013.01); *A61Q 5/02* (2013.01); *A61K 2800/596* (2013.01)

(58) Field of Classification Search
CPC ... C11D 3/30; A61K 8/34; A61K 8/41; A61K 8/42; A61K 8/44; A61K 8/46; A61K 8/60; A61K 8/86; A61Q 5/02
See application file for complete search history.

(56) References Cited

U.S. PATENT DOCUMENTS

| | | | |
|---|---|---|---|
| 10,507,177 B1 * | 12/2019 | Kawa | A61Q 5/002 |
| 2003/0012761 A1 | 1/2003 | Yoshida et al. | |
| 2006/0068390 A1 | 3/2006 | Tillett et al. | |
| 2013/0101543 A1 | 4/2013 | Tamareselvy et al. | |
| 2013/0109611 A1 | 5/2013 | O'Connor et al. | |
| 2013/0115185 A1 | 5/2013 | Tamareselvy et al. | |
| 2014/0255456 A1 | 9/2014 | Cohen | |
| 2015/0157540 A1 * | 6/2015 | Rizk | A61K 8/39 510/122 |
| 2015/0157548 A1 | 6/2015 | De Feij et al. | |
| 2018/0042828 A1 | 2/2018 | Cohen | |
| 2018/0055748 A1 | 3/2018 | Cohen | |
| 2018/0098923 A1 | 4/2018 | Hutton, III | |
| 2018/0280270 A1 | 10/2018 | Rughani et al. | |
| 2019/0099342 A1 | 4/2019 | Kuper et al. | |
| 2019/0282480 A1 | 9/2019 | Su et al. | |
| 2019/0328641 A1 | 10/2019 | Kelada et al. | |
| 2019/0365619 A1 * | 12/2019 | Ceballos | A61K 8/466 |
| 2019/0365623 A1 | 12/2019 | Botto et al. | |
| 2020/0276099 A1 | 9/2020 | Robbins et al. | |
| 2021/0212927 A1 | 7/2021 | Hutton, III et al. | |
| 2021/0220243 A1 | 7/2021 | Hiban et al. | |
| 2021/0299013 A1 | 9/2021 | Day et al. | |
| 2021/0401716 A1 | 12/2021 | Gogineni et al. | |

FOREIGN PATENT DOCUMENTS

| | | | | |
|---|---|---|---|---|
| CN | 103356408 | A | 10/2013 | |
| CN | 104739718 | A | 7/2015 | |
| CN | 104997661 | | * 10/2015 | ............... A61K 8/97 |
| CN | 104997661 | A | 10/2015 | |
| CN | 105616269 | A | 6/2016 | |
| CN | 106361660 | A | 2/2017 | |
| CN | 107898687 | A | 4/2018 | |
| CN | 109481352 | A | 3/2019 | |
| CN | 109498494 | A | 3/2019 | |
| CN | 112137951 | A | 12/2020 | |
| DE | 102015223454 | A1 | 6/2016 | |
| DE | 102018202804 | A1 | 8/2019 | |
| KR | 20130055386 | A | 5/2013 | |
| KR | 20130055387 | A | 5/2013 | |
| KR | 20170104849 | A | 9/2017 | |
| WO | 2013098066 | A2 | 7/2013 | |
| WO | 2013113536 | A1 | 8/2013 | |
| WO | 2013149873 | A2 | 10/2013 | |
| WO | 2017106276 | A1 | 6/2017 | |
| WO | 2019074989 | A1 | 4/2019 | |

OTHER PUBLICATIONS

Preliminary Search Report and Written Opinion issued on Apr. 5, 2022 for corresponding French Application No. FR 2107844.
Database GNPD [Online] Anonymous: "Botanical Shampoo," 2020 XP055908368.
Non-Final Rejection issued on Jun. 7, 2022 for co-pending U.S. Appl. No. 17/008,135.
Final Rejection issued on Mar. 9, 2023 for co-pending U.S. Appl. No. 17/008,135.
Non-Final Rejection issued on Jan. 10, 2024 for co-pending U.S. Appl. No. 17/008,135.
Final Rejection issued on Jun. 13, 2024 for co-pending U.S. Appl. No. 17/008,135.
International Preliminary Report on Patentability and Written Opinion for corresponding PCT Application No. PCT/US201/046740, dated Feb. 28, 2023.
International Search Report and Written Opinion for corresponding PCT Application No. PCT/US201/046740, dated Nov. 24, 2021.
U.S. Appl. No. 17/008,135, filed Aug. 31, 2020.

* cited by examiner

CLEANSING COMPOSITIONS

CROSS-REFERENCE TO RELATED APPLICATIONS

This application claims benefit of U.S. Ser. No. 63/143,278, filed Jan. 29, 2021, and benefit of French Application Serial No. FR 2107844, filed on Jul. 21, 2021, which are incorporated herein by reference in their entirety.

FIELD OF THE DISCLOSURE

The present disclosure relates to cleansing compositions and, particularly, hair cleansing compositions that include a limited amount of anionic surfactants and/or silicones.

BACKGROUND OF THE DISCLOSURE

Conventional personal care cleansing compositions such as shampoo, body wash, facial cleanser, hand soap, etc., typically use sulfate-based surfactants such as sodium lauryl sulfate (SLS) or sodium laureth ether sulfate (SLES). These surfactants are commonly used because they have good foaming and cleansing properties, can be thickened easily, and are relatively inexpensive.

Silicones are also commonly used in personal care products for their conditioning and cosmetic effects. For example, silicones provide a protective layer on the hair which allows the hair to be easily detangled and combed, and providing smoothness and glossiness. However, silicones can build up on hair layer-by-layer, which can weigh down the hair and make the hair greasy. Furthermore, silicones are not easily degraded, and accordingly their use in personal care products raises environmental concerns.

Furthermore, consumers desire natural compositions for personal care products such as compositions for cleansing hair and skin. There is an increased demand for sustainable, safe, and environmentally friendly "green" compositions that are free of or essentially free of silicones, as well as other synthetic chemical materials for cleansing and/or caring cleansing keratin materials, including hair and skin, and yet provide desirable overall good performance and high safety. However, such "green" compositions are often expensive to produce as their materials must be sourced from natural sources such as plants, as opposed to being high-volume, industrially-produced chemicals. Moreover, it is often difficult to achieve an acceptable balance of desirable cleansing composition performance properties when using naturally-sourced products. For example, the addition of a particular component to a cleansing composition will often enhance one desired property to the detriment of another desired property.

Additionally, there are challenges in developing suitable formulations of cleansing products without the use of sulfate-based surfactants such as sulfate-based anionic surfactants, and/or silicones ("sulfate-free" and/or "silicone-free"). For example, most existing sulfate-free hair cleansing products foam poorly, are opaque, and are not easily thickened. Traditional methods of increasing viscosity of these formulations, such as incorporation of a salt, are not effective with sulfate-free surfactants.

SUMMARY OF THE DISCLOSURE

Aspects of the disclosure relate to cleansing compositions and, particularly, hair cleansing compositions that include a limited amount of anionic surfactants and/or silicones. For instance, the cleansing compositions may include limited amounts of anionic surfactants, and specifically, anionic sulfate surfactants. In some embodiments, the cleansing compositions are substantially free or free of anionic sulfate surfactants. The cleansing compositions may be formulated to be free or substantially free of silicones.

The cleansing compositions may be formulated as shampoo compositions. Shampoo compositions according to aspects of the disclosure typically include:
(a) about 6 wt. % or more of one or more betaine surfactants;
(b) about 5 wt. % or less of one or more anionic surfactants;
(c) about 0.1 wt. % to about 10 wt. % of one or more fatty amine surfactants;
(d) about 0.1 to about 15 wt. % of one or more nonionic surfactants, wherein at least one of the one or more nonionic surfactants is chosen from alkoxylated nonionic surfactants;
wherein the shampoo composition has a weight ratio of the total amount of (a) to the total amount of (b)+(c)+(d) of 0.8:1 to 5:1; and
(e) water;
wherein the shampoo composition is substantially free of anionic sulfate surfactants;
the shampoo composition is substantially free of silicones; and
all weight percentages are based on the total weight of the shampoo composition.

The one or more betaine surfactants may be chosen from cocamidopropyl betaine, coco-betaine, or a mixture thereof. In some cases, the shampoo composition may have about 6 to about 20 wt. % of two or more betaine surfactants. For example, the two or more betaine surfactants in the shampoo composition may be cocamidopropyl betaine and coco-betaine.

Additionally or alternatively, the shampoo composition may include one or more non-sulfate anionic surfactants that are chosen from amino acid surfactants, isethionate surfactants, or a mixture thereof. In at least one instance, the one or more non-sulfate anionic surfactants is chosen from amino acid surfactants. In at least one other instance, the one or more non-sulfate anionic surfactants is chosen from isethionate surfactants.

The shampoo composition may be formulated to have a pH of about 4 up to 7. Preferably, at least a portion of the fatty amine is emulsified and not acid neutralized. The fatty amine may be an amidoamine that is chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palm itam idopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, m inkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palm itam idopropyl dimethylamine, stearamidoethyldiethylamine, and a mixture thereof.

Non-limiting examples of the one or more nonionic surfactants include those chosen from PEG-55 propylene glycol oleate, PEG-6 propylene glycol caprylate/caprate, PEG-8 propylene glycol cocoate, PEG-25 propylene glycol stearate, PEG-7 glyceryl cocoate, PEG-30 glyceryl cocoate, laureth-2, laureth-3, laureth-4, PEG-200 glyceryl stearate, PEG-120 propylene glycol stearate, and a mixture thereof. In at least one embodiment, the one or more nonionic surfactants comprises a glucoside.

The shampoo composition may also comprise about 0.1 to about 10 wt. % of one or more polyols chosen from ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, glycerin, diglycerin, caprylyl glycol, and a mixture thereof.

In some cases, the shampoo composition is transparent. The shampoo composition may also be formulated to contain about 90% or more, by weight, of all compounds that are biodegradable according to OECD Test Guidelines No. 301 A, B, C, D, E, and/or F. Additionally or alternatively, the total amount of (a) is greater than the total amount of (d).

According to another aspect of the disclosure, provided is a method for cleansing hair comprising applying a shampoo composition to the hair, and rinsing the shampoo composition from the hair, wherein the shampoo composition comprises:
(a) about 6 wt. % or more of one or more betaine surfactants;
(b) about 5 wt. % or less of one or more anionic surfactants;
(c) about 0.1 wt. % to about 10 wt. % of one or more fatty amine surfactants;
(d) about 0.1 to about 10 wt. % of one or more nonionic surfactants wherein at least one of the one or more nonionic surfactants is chosen from alkoxylated nonionic surfactants;
wherein the shampoo composition has a weight ratio of the total amount of (a) to the total amount of (b)+(c)+(d) of 0.8:1 to 5:1; and
(e) water;
wherein the shampoo composition is substantially free of anionic sulfate surfactants;
the shampoo composition is substantially free from silicones; and
all weight percentages are based on the total weight of the shampoo composition.

BRIEF DESCRIPTION OF FIGURES

Implementation of the present technology will now be described, by way of example only, with reference to the attached figures, wherein.

Figure 1:
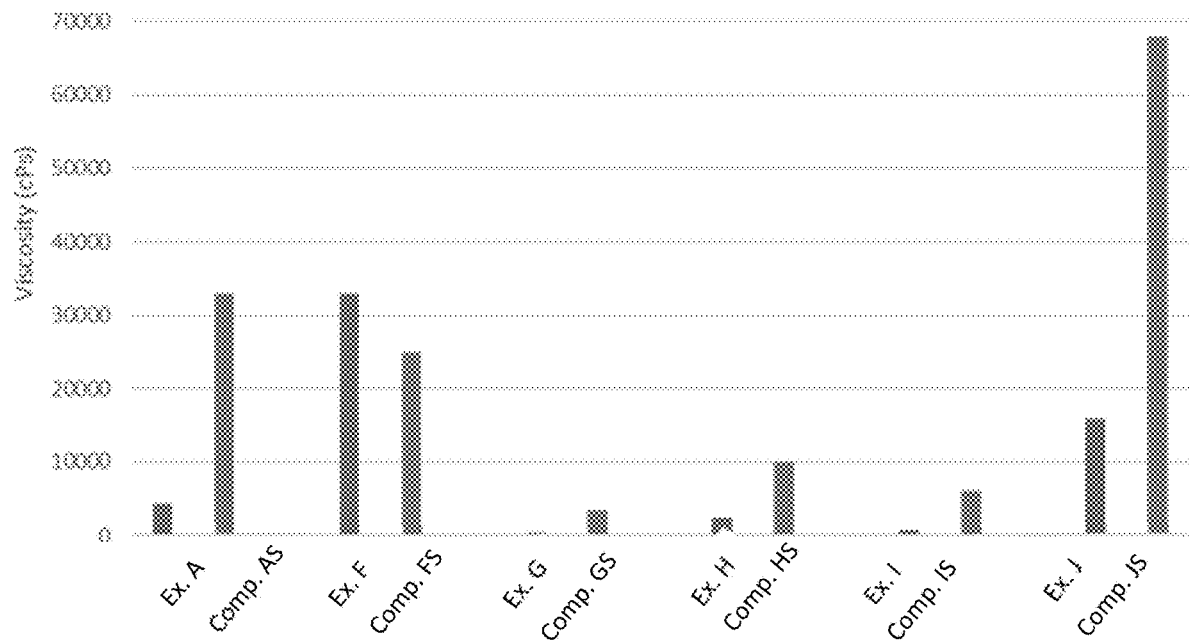
FIG. 1 is a bar graph showing the effect of PEGylated surfactants and sebum on the viscosity of cleansing compositions according to an aspect of the disclosure.

It should be understood that the various aspects are not limited to the arrangements and instrumentality shown in the drawings.

DETAILED DESCRIPTION OF THE DISCLOSURE

Aspects of the disclosure relate to cleansing compositions and, particularly, hair cleansing compositions that include a limited amount of anionic surfactants and/or silicones. The inventors recognized that cleansing compositions containing particular compounds in certain amounts and ratios advantageously enable a reduction in the amount of anionic surfactants, specifically anionic sulfate surfactants, while providing desirable cleansing, detangling, and combining properties. For instance, the cleansing compositions may be formulated to have a weight ratio of the total amount of betaine surfactants to the total amount of anionic surfactants, fatty amine surfactants, and nonionic surfactants that is 0.8:1 to 5:1. In some cases, the cleansing composition has an amount of betaine surfactants that is greater than the total amount of nonionic surfactants.

The cleansing compositions may be formulated with reduced amounts of anionic surfactants, such as about 5 wt. % or less of anionic surfactants. The total amount of anionic surfactants in the cleansing compositions may be about 5 wt. % or less, about 4.75 wt. % or less, about 4.5 wt. % or less, about 4.25 wt. % or less, about 4 wt. % or less, about 3.75 wt. % or less, about 3.5 wt. % or less, about 3.25 wt. % or less, about 3 wt. % or less, about 2.75 wt. % or less, about 2.5 wt. % or less, about 2.25 wt. % or less, about 2 wt. % or less, about 1.75 wt. % or less, about 1.5 wt. % or less, about 1.25 wt. % or less, about 1 wt. % or less, about 0.75 wt. % or less, about 0.5 wt. % or less, or about 0.25 wt. % or less. In at least one embodiment, the cleansing composition contains about 0 wt. % or 0 wt. % of anionic sulfate surfactants. Additionally or alternatively, the cleansing compositions may be substantially free or free of anionic sulfate surfactants. For example, the cleansing compositions may have about 5 wt. % or less, about 4.75 wt. % or less, about 4.5 wt. % or less, about 4.25 wt. % or less, about 4 wt. % or less, about 3.75 wt. % or less, about 3.5 wt. % or less, about 3.25 wt. % or less, about 3 wt. % or less, about 2.75 wt. % or less, about 2.5 wt. % or less, about 2.25 wt. % or less, about 2 wt. % or less, about 1.75 wt. % or less, about 1.5 wt. % or less, about 1.25 wt. % or less, about 1 wt. % or less, about 0.75 wt. % or less, about 0.5 wt. % or less, about 0.25 wt. % or less, about 0.15 wt. % or less, about 0.1 wt. % or less, about 0.05 wt. % or less, or about 0.01 wt. % or less of anionic sulfate surfactants. In at least one instance, the cleansing compositions contains no anionic sulfate surfactants.

Anionic sulfate surfactants are typically alkyl sulfates, alkyl ether sulfates, and/or salts thereof and may include $C_{8-18}$ alkyl sulfates, such as $C_{12-18}$ alkyl sulfates, that may be in the form of a salt with a solubilizing cation such as sodium, potassium, ammonium or substituted ammonium. Alkyl ether sulfates include those having the formula: $RO(CH_2CH_2O)_nSO_3M$; wherein R is an alkyl or alkenyl having from 8 to 18 (; n is a number having an average value of greater than at least 0.5; and M is a solubilizing cation such as sodium, potassium, ammonium or substituted ammonium. Examples of anionic sulfate surfactants are sodium lauryl ether sulfate (SLES) and sodium lauryl sulfate (SLS).

In some instances, the cleansing compositions may be formulated to be free or substantially free of silicones. The cleansing compositions may have, e.g., about 5 wt. % or less, about 4.5 wt. % or less, about 4 wt. % or less, about 3.5 wt. % or less, about 3 wt. % or less, about 2.5 wt. % or less, about 2 wt. % or less, about 1.5 wt. % or less, about 1 wt. % or less, about 0.5 wt. % or less. In at least one embodiment, the cleansing compositions have no silicones.

Advantageously, the cleansing compositions may be formulated as "green" compositions that include biodegradable compounds/ingredients. For example, about 90% or more, by weight, of all compounds of the cleansing compositions may be biodegradable according to OECD Test Guidelines No. 301 A, B, C, D, E, and/or F. See OECD Guidelines for Testing of Chemicals: Ready Biodegradability, available at https://www.oecd-ilibrary.org/docserver/9789264070349-en.pdf?expires=1611606648&id=id&accname=guest&checksum=29E51E8E7A2187C7 69B4AEEA2FB29175 (adopted Jul. 17, 1992), which is incorporated herein in its entirety for all purposes. In some cases, the cleansing compositions are formulated to have about 91 wt. % or more, about 92 wt. % or more, about 93 wt. % or more, about 94 wt. % or more, about 95 wt. % or more, about 95.5 wt. % or more, about 96 wt. % or more, about 96.5 wt. % or more, about 97 wt. % or more, about 97.5 wt. % or more, about 98 wt. % or more, about 98.5 wt. % or more, about 99 wt. % or more, about 99.5 wt. % or more, or up to 100 wt. %, including any ranges and subranges therebetween, of all the compounds in the cleansing composition that are biodegradable according to OECD Test Guidelines No. 301 A, B, C, D, E, and/or F.

The cleansing compositions may be formulated as shampoo compositions. Shampoo compositions according to aspects of the disclosure typically include:
  (a) about 6 wt. % or more of one or more betaine surfactants;
  (b) about 5 wt. % or less of one or more anionic surfactants;
  (c) about 0.1 wt. % to about 10 wt. % of one or more fatty amine surfactants;
  (d) about 0.1 to about 15 wt. % of one or more nonionic surfactants, wherein at least one of the one or more nonionic surfactants is chosen from alkoxylated nonionic surfactants;
    wherein the shampoo composition has a weight ratio of the total amount of (a) to the total amount of (b)+(c)+(d) of 0.8:1 to 5:1; and
  (e) water;
    wherein the shampoo composition is substantially free of anionic sulfate surfactants;
    the shampoo composition is substantially free of silicones; and
    all weight percentages are based on the total weight of the shampoo composition.

In some cases, the weight ratio of the total amount of betaine surfactants to the total amount of anionic surfactants, fatty amine surfactants, and nonionic surfactants is 0.8:1 to 5:1, 0.85:1 to 5:1, 0.9:1 to 5:1, 0.95:1 to 5:1, 1:1 to 5:1; 0.8:1 to 4:1, 0.85:1 to 4:1, 0.9:1 to 4:1, 0.95:1 to 4:1, 1:1 to 4:1; 0.8:1 to 3:1, 0.85:1 to 3:1, 0.9:1 to 3:1, 0.95:1 to 3:1, 1:1 to 3:1; 0.8:1 to 2:1, 0.85:1 to 2:1, 0.9:1 to 2:1, 0.95:1 to 2:1, 1:1 to 2:1, 1.1:1 to 3:1, 1.1:1 to 2.7:1, or any range or subrange therebetween. Additionally or alternatively, the total amount amphoteric surfactants or betaine surfactants are the predominant type of surfactant in the surfactant system, i.e., there is a higher percentage of amphoteric surfactants than any other single type of surfactant in the composition. Moreover, in some instances, the total amount of amphoteric surfactants and/or betaine surfactants in the surfactant system is higher than the total amount of all other surfactant types in the surfactant system. In other words, the phrase "all other surfactants" means any and all surfactants in the cleansing composition other than amphoteric surfactants and/or betaine surfactants.

In at least some cases, the cleansing/shampoo composition may have a weight ratio of the total amount of betaine surfactants to the total amount of non-sulfate anionic surfactants of about 3:1 to about 16:1, about 4:1 to about 16:1, about 5:1 to about 16:1, about 6:1 to about 16:1, about 7:1 to about 16:1, about 8:1 to about 16:1, about 9:1 to about 16:1, about 10:1 to about 16:1, about 11:1 to about 16:1, about 12:1 to about 16:1; about 3:1 to about 14:1, about 4:1 to about 14:1, about 4.1:1 to about 14:1, about 4.2:1 to about 14:1, about 4.3:1 to about 14:1, about 4.4:1 to about 14:1, about 4.5:1 to about 14:1, about 4.6:1 to about 14:1, about 4.7:1 to about 14:1, about 4.8:1 to about 14:1, about 4.9:1 to about 14:1, about 5:1 to about 14:1, about 6:1 to about 14:1, about 7:1 to about 14:1, about 8:1 to about 14:1, about 9:1 to about 14:1, about 10:1 to about 14:1, about 11:1 to about 14:1, about 12:1 to about 14:1; about 3:1 to about 12:1, about 4:1 to about 12:1, about 4.5:1 to about 12:1, about 4.6:1 to about 12:1, about 4.7:1 to about 12:1, about 4.8:1 to about 12:1, about 4.9:1 to about 12:1, about 5:1 to about 12:1, about 6:1 to about 12:1, about 7:1 to about 12:1, about 8:1 to about 12:1, about 9:1 to about 12:1, about 10:1 to about 12:1; about 3:1 to about 10:1, about 4:1 to about 10:1, about 4.5:1 to about 10:1, about 4.6:1 to about 10:1, about 4.7:1 to about 10:1, about 4.8:1 to about 10:1, about 4.9:1 to about 10:1, about 5:1 to about 10:1, about 6:1 to about 10:1, about 7:1 to about 10:1, about 8:1 to about 10:1; about 3:1 to about 8:1, about 4:1 to about 8:1, about 4.5:1 to about 8:1, about 4.6:1 to about 8:1, about 4.7:1 to about 8:1, about 4.8:1 to about 8:1, about 4.9:1 to about 8:1, about 5:1 to about 8:1, about 6:1 to about 8:1; about 3:1 to about 6:1, or about 4:1 to about 6:1.

The cleansing/shampoo composition may be transparent. The term "transparent" with respect to a transparent composition indicates that the composition has transmittance of at least 80% at a wavelength of 600 nm, for example measured using a Lambda 40 UV-visible spectrometer. The cleansing compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure.

In some cases, the cleansing compositions may be formulated to, additionally or alternatively, be substantially free of or free of oil and/or alcohol. In some embodiments, a composition is devoid of oil. Those of skill in the art will appreciate that oil may be present in the cleansing compositions via its presence in one or more of the ingredients; thus, in some embodiments a composition may be substantially free of oil. For instance, oil may be present at a concentration that does not exceed 5 wt. %, and in some instances is present not more than 3 wt. %, and in some instances is present not more than 1 wt. %, based on the weight of the cleansing composition.

In some embodiments, a composition is devoid of alcohol. Those of skill in the art will appreciate that alcohol may be present in a composition via its presence in one or more of the ingredients; thus, in some embodiments the cleansing composition may be substantially free of alcohol. For example, alcohol may be present in the cleansing composition at a concentration that does not exceed 5 wt. %, and in some instances is present not more than 3 wt. %, and in some instances is present not more than 1 wt. %, based on the total weight of the cleansing composition.

The cleansing composition may, optionally, include about 10 wt. % or less of miscellaneous ingredients, based on the total weight of the cleansing composition. Non-limiting examples of miscellaneous ingredients include active ingredients, pH adjusters, preservatives, salts, chelating agent, colorants, salts, antimicrobial agents, fragrances, vitamins, pearlescent agents, odor absorbers, coloring materials, essential oils, fruit extracts, and combinations thereof. One or more of the foregoing miscellaneous ingredients may be excluded from embodiments of the disclosure. The amount of miscellaneous ingredients may be about 10 wt. % or less, about 9 wt. % or less, about 8 wt. % or less, about 7 wt. % or less, about 6 wt. % or less, about 5 wt. % or less, about 4 wt. % or less, about 3 wt. % or less, about 2 wt. % or less, or about 1 wt. % or less, based on the total weight of the cleansing composition.

The cleansing compositions may have a viscosity of about 1,000 to about 10,000 cPs at a temperature of 24° C. as measured with RV-4 Disk spindle on a Brookfield DV2T viscometer at a range of 5-20 rpm after 90 seconds. For instance, the cleansing compositions may have a viscosity in the range of about 1,000 to about 10,000 cPs, about 1,000 to about 9,000 cPs, about 1,000 to about 8,000 cPs, about 1,000 to about 7,000 cPs, about 1,000 to about 6,000 cPs, about 1,000 to about 5,000 cPs, about 1,000 to about 4,000 cPs; about 2,000 to about 10,000 cPs, about 2,000 to about 9,000 cPs, about 2,000 to about 8,000 cPs, about 3,000 to about 8,000 cPs, about 3,000 to about 7,000 cPs, about 2,000 to about 6,000 cPs, about 2,000 to about 5,000 cPs, about 2,000 to about 4,000 cPs; about 3,000 to about 10,000 cPs, about 3,000 to about 9,000 cPs, about 3,000 to about 8,000 cPs, about 3,000 to about 7,600 cPs, about 3,000 to about 6,000 cPs, about 3,000 to about 5,000 cPs; about 4,000 to about 10,000 cPs, about 4,000 to about 9,000 cPs, about 4,000 to about 8,000 cPs, about 4,000 to about 7,000 cPs, about 4,000 to about 6,000 cPs; about 5,000 to about 10,000 cPs, about 5,000 to about 9,000 cPs, about 5,000 to about 8,000 cPs, about 5,000 to about 7,000 cPs; about 6,000 to about 10,000 cPs, about 6,000 to about 9,000 cPs, about 6,000 to about 8,000 cPs; about 7,000 to about 10,000 cPs, about 7,000 to about 9,000 cPs, at a temperature of 24° C. as measured with RV-4 Disk spindle on a Brookfield DV2T viscometer at a range of 5-20 rpm after 90 seconds.

Suitable components, such as those listed below, may be included or excluded from the formulations for the cleansing compositions depending on the specific combination of other components, the form of the cleansing compositions, and/or the use of the formulation (e.g., a shampoo).

Betaine Surfactant(s)

The cleansing compositions include one or more betaine surfactants in an amount that may vary, but is typically about 6 wt. % or more, based on the total weight of the cleansing composition. For example, the cleansing compositions may include one or more betaine surfactants in an amount of about 6 wt. % or more, about 6.5 wt. % or more, about 7 wt. % or more, about 7.5 wt. % or more, about 8 wt. % or more, about 8.5 wt. % or more, about 9 wt. % or more, about 9.5 wt. % or more, about 10 wt. % or more, or 10.5 wt. % or more, based on the total weight of the cleansing composition. In some cases, the cleansing compositions include betaine surfactants in an amount of about 6 to about 25 wt. %, about 6 to about 22 wt. %, about 6 to about 20 wt. %, about 6 to about 18 wt. %, about 6 to about 16 wt. %, about 6 to about 14 wt. %, about 6 to about 12 wt. %, about 6 to about 10 wt. %, about 6 to about 9 wt. %, or about 6 to about 8 wt. %; about 7 to about 25 wt. %, about 7 to about 22 wt. %, about 7 to about 20 wt. %, about 7 to about 18 wt. %, about 7 to about 16 wt. %, about 7 to about 14 wt. %, about 7 to about 12 wt. %, about 7 to about 10 wt. %, or about 7 to about 9 wt. %; about 8 to about 25 wt. %, about 8 to about 22 wt. %, about 8 to about 20 wt. %, about 8 to about 18 wt. %, about 8 to about 16 wt. %, about 8 to about 14 wt. %, about 8 to about 12 wt. %, about 8 to about 10 wt. %, or about 8 to about 9 wt. %, based on the total weight of the cleansing composition.

Preferably, the cleansing composition includes two or more betaine surfactants. For example, the cleansing composition may include two betaine surfactants, three betaine surfactants, four betaine surfactants, five betaine surfactants, or six betaine surfactants, etc. The ratio of the amount of the at least one first betaine surfactant to the amount of the at least one second betaine surfactant may range from about 1:10 to about 10:1. For example, the ratio of the amounts of the first betaine surfactant to the second betaine surfactant may be about 1:10, about 1:9, about 1:8, about 1:7, about 1:6, about 1:5, about 1:4, about 1:3, about 1:2, about 1:1, or any range or subrange therebetween.

The one or more betaine surfactants may be in the form of a salt in the cleansing composition or before addition to the cleansing composition. The betaine surfactants may be derived from a variety of natural oils or fatty acids.

In some embodiments, exemplary useful betaines include, but are not limited to, those of the following formulae (Ia-Id):

(Ia)

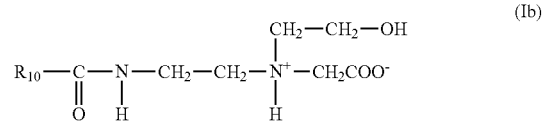

(Ib)

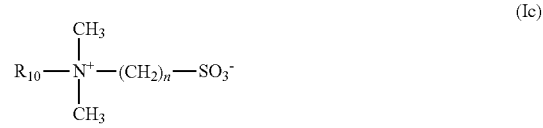

(Ic)

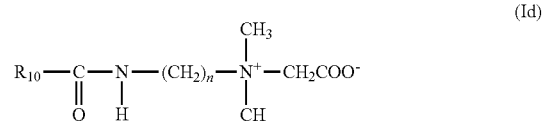

(Id)

wherein:

$R_{10}$ is an alkyl group having from 8-18 carbon atoms; and n is an integer from 1 to 3.

Particularly useful betaines include, for example, cocobetaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or mixtures thereof. Typically, at least one betaine compound is selected from coco betaine, cocamidopropyl betaine, behenyl betaine, capryl/capramidopropyl betaine, and lauryl betaine, and mixtures thereof. In one embodiment, preferred betaines include coco-betaine and cocamidopropyl betaine.

Non-Betaine Amphoteric Surfactant(s)

The cleansing compositions may optionally include one or more amphoteric surfactants that is not a betaine surfactant. The non-betaine amphoteric surfactants, if present, may be included in the cleansing compositions in an amount of about 0.1 to about 15 wt. %, about 0.1 to about 10 wt. %, about 0.1 to about 8 wt. %, or about 0.1 to about 6 wt. %; about 0.5 to about 15 wt. %, about 0.5 to about 10 wt. %, about 0.5 to about 8 wt. %, or about 0.5 to about 6 wt. %; about 1 to about 15 wt. %, about 1 to about 10 wt. %, about 1 to about 8 wt. %, or about 1 to about 6 wt. %; about 1.5 to about 15 wt. %, about 1.5 to about 10 wt. %, about 1.5 to about 8 wt. %, or about 1.5 to about 6 wt. %; or about 2 to about 15 wt. %, about 2 to about 10 wt. %, about 2 to about 8 wt. %, or about 2 to about 6 wt. %, including all ranges and subranges therebetween, based on the total weight of the cleansing composition.

The cleansing composition may comprise a non-betaine amphoteric surfactant chosen from alkyl amphoacetates, alkyl amphodiacetates, alkyl sulltaines, alkyl amphopropionates or salts thereof. Further discussion of non-limiting examples of alkyl amphoacetates, alkyl amphodiacetates, alkyl sulltaines, and alkyl amphopropionates are disclosed below.

(a) Alkyl Amphoacetates and Alkyl Amphodiacetates

By way of example only, useful alkyl amphoacetates and alkyl amphodiacetates include those of Formula (IIa) or (IIb):

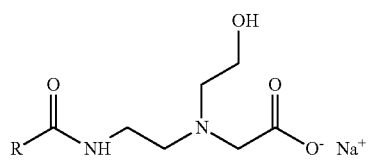

(IIa)

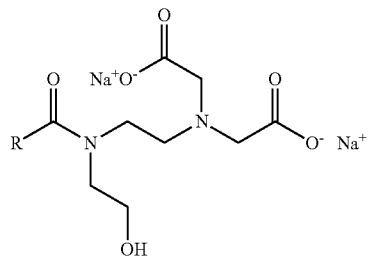

(IIb)

wherein R is an alkyl group having 8-18 carbon atoms.

Although sodium is shown as the cation in the above formulae, the cation may be any alkali metal ion, such as sodium or potassium, an ammonium ion, or an alkanolammonium ion such as monoethanolammonium or triethanolammonium ions. A non-limiting example is sodium lauroamphoacetate.

Additional non-limiting examples of alkyl amphoacetates and alkyl amphodiacetates include those of formula (IIc):

$Ra'$—CON(Z)CH2—(CH2)$m'$—N(B)(B')     (IIc)

wherein:
B represents —CH2CH2OX', with X' representing —CH2—COOH, CH2—COOZ', —CH2CH2—COOH, —CH2CH2—COOZ', or a hydrogen atom;
B' represents —CH2)z—Y', with z=1 or 2, and Y' representing —COOH, —COOZ', —CH2—CHOH—SO3H or —CH2—CHOH—SO3Z';
m' is equal to 0, 1 or 2;
Z represents a hydrogen atom or a hydroxyethyl or carboxymethyl group;
Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanol-amine, diisopropanolamine or triisopropanolamine, 2-amino-2-methyl-1-propanol, 2-amino-2-methyl-1,3-propanediol and tris (hydroxy-methyl)aminomethane; and
Ra' represents a (C10-C30)alkyl or alkenyl group of an acid Ra'COOH preferably present in hydrolyzed linseed oil or coconut oil, an alkyl group, in particular a C17 alkyl group, and its iso form, or an unsaturated C17 group.

Exemplary compounds of formula (Ic) include (C8-C20) alkylamphoacetates and (C8-C20)alkylamphodiacetates, such as disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylomphodipropionate, lauroamphodipropionic acid, or cocoamphodipropionic acid. For example, disodium cocoamphodiacetate supplied by Rhodia under the name MIRANOLI $C_2M$ can be used.

(b) Alkyl Sulltaines

Non-limiting examples of alkyl sultaines include hydroxyl sultaines of the following formula (IId)

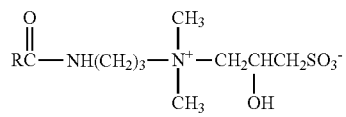

(IId)

wherein R is an alkyl group having 8-18 carbon atoms. More specific examples include, but are not limited to cocamidopropyl hydroxysultaine, lauryl hydroxysultaine, and a mixture thereof.

(c) Alkyl Amphopropionates

Non-limiting examples of alkyl amphopropionates include cocoamphopropionate, cornamphopropionatecaprylamphopropionate, cornamphopropionate, caproamphopropionate, oleoamphopropionate, isostearoamphopropionate, stearoamphopropionate, lauroamphopropionate, salts thereof, and a mixture thereof.

Non-Sulfate Anionic Surfactant(s)

The cleansing compositions typically include anionic surfactants in an amount of about 5 wt. % or less, based on the total weight of the cleansing composition. For example, the amount of anionic surfactants if present in the cleansing compositions may be about 4.75 wt. % or less, about 4.5 wt. % or less, about 4.25 wt. % or less, about 4 wt. % or less, about 3.75 wt. % or less, about 3.5 wt. % or less, about 3.25 wt. % or less, about 3 wt. % or less, about 2.75 wt. % or less, 2.5 wt. % or less, 2.25 wt. % or less, 2 wt. % or less, 1.75 wt. % or less, 1.5 wt. % or less, 1.25 wt. % or less, 1 wt. % or less, 0.75 wt. % or less, 0.5 wt. % or less, 0.25 wt. % or less, based on the total weight of the cleansing composition. In some cases, the amount of anionic surfactant may be about 0.01 to about 5 wt. %, about 0.01 to about 4.5 wt. %, about 0.01 to about 4 wt. %, about 0.01 to about 3.5 wt. %, about 0.01 to about 3 wt. %, about 0.01 to about 2.5 wt. %, about 0.01 to about 2 wt. %, about 0.01 to about 1.5 wt. %, about 0.01 to about 1 wt. %, or about 0.01 to about 0.5 wt. %; about 0.1 to about 5 wt. %, about 0.1 to about 4.5 wt. %, about 0.1 to about 4 wt. %, about 0.1 to about 3.5 wt. %, about 0.1 to about 3 wt. %, about 0.1 to about 2.5 wt. %, about 0.1 to about 2 wt. %, about 0.1 to about 1.5 wt. %, about 0.1 to about 1 wt. %, or about 0.1 to about 0.5 wt. %; about 0.2 to about 5 wt. %, about 0.2 to about 4.5 wt. %, about 0.2 to about 4 wt. %, about 0.2 to about 3.5 wt. %, about 0.2 to about 3 wt. %, about 0.2 to about 2.5 wt. %, about 0.2 to about 2 wt. %, about 0.2 to about 1.5 wt. %, about 0.2 to about 1 wt. %, or about 0.2 to about 0.5 wt. %; about 0.5 to about 5 wt. %, about 0.5 to about 4.5 wt. %, about 0.5 to about 4 wt. %, about 0.5 to about 3.5 wt. %, about 0.5 to about 3 wt. %, about 0.5 to about 2.5 wt. %, about 0.5 to about 2 wt. %, about 0.5 to about 1.5 wt. %, or about 0.5 to about 1 wt. %; about 1 to about 5 wt. %, about 1 to about 4.5 wt. %, about 1 to about 4 wt. %, about 1 to about 3.5 wt. %, about 1 to about 3 wt. %, about 1 to about 2.5 wt. %, about 1 to about 2 wt. %, or about 1 to about 1.5 wt. %, including ranges and subranges therebetween, based on the total weight of the cleansing composition.

Although the cleansing composition may be formulated without anionic surfactants containing a sulfate group, in some embodiments of the disclosure the cleansing composition includes one or more anionic surfactants containing a sulfate group. For example, in at least one embodiment, cleansing composition includes anionic sulfate surfactants such as sodium lauryl sulfate (SLS) or sodium laureth ether sulfate (SLES).

Preferably, the anionic surfactants, if present, in the cleansing composition are non-sulfate anionic surfactants. Useful non-sulfate anionic surfactants include, but are not limited to, alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, and a mixture thereof. In some cases, however, acyl taurates are preferred and therefore the one or more non-sulfate anionic surfactants include at least one acyl taurate. It is also preferable, in some instances, to include two or more acyl taurates in the cleansing compositions. Thus, the cleansing compositions may include one or more non-sulfate anionic surfactants wherein at least one (and preferably two or more) of the anionic surfactants are selected from acyl taurates. In other cases, acyl isethionates are preferred and therefore the one or more non-sulfate anionic surfactants include at least one acyl isethionate. It is also preferable, in some instances, to include two or more acyl isethionates in the cleansing compositions. Thus, the cleansing compositions may include one or more non-sulfate anionic surfactants wherein at least one (and preferably two or more) of the anionic surfactants are selected from acyl isethionates.

In yet other cases, a combination of acyl taurates and acyl isethionates may be used. Thus, the cleansing compositions may include two or more non-sulfate anionic surfactants comprising anionic surfactants selected from acyl taurates and acyl isethionates.

Non-limiting examples of non-sulfate anionic surfactants are provided below.

(a) Acyl Isethionates

Non-limiting examples of useful acyl isethionates include those of formula (III) and (IV):

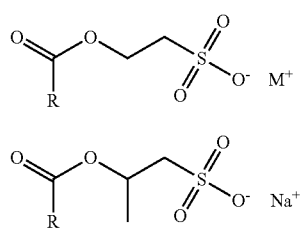

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Although sodium is shown as the cation in formulae (III) and (IV), the cation for both formula (III) and formula (IV) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some embodiments, a combination of sodium isethionate and sodium cocoyl isethionate are preferable.

(b) Alkyl Sulfonates

Examples of alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (V) is particularly useful.

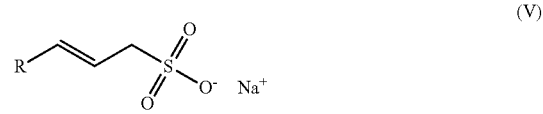

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (V) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and mixtures thereof. $C_{10}$-$C_{24}$ olefin sulfonates may be particularly preferred. A non-limiting example of a $C_{10}$-$C_{24}$ olefin sulfonate that can be used in the instant compositions is sodium $C_{14}$-$C_{16}$ olefin sulfonate.

(c) Alkyl Sulfosuccinates

Non-limiting examples of useful sulfosuccinates include those of formula (VI):

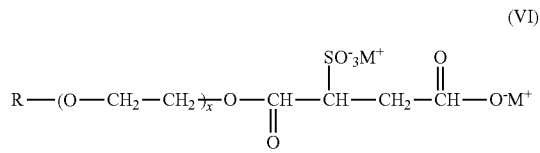

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof. In some instances, disodium laureth sulfosuccinate is particularly preferred.

(d) Alkyl Sulfoacetates

Non-limiting examples of alkyl sulfacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

(e) Alkoxylated Monoacids

Non-limiting examples of alkoxylated monoacids include compounds corresponding to formula (VII):

$$RO[CH2O]u[(CH2)xCH(R')(CH2)y(CH2)zO]v[CH2CH2O]wCH2COOH \quad (VII)$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z>0;

Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic $C_6$-$C_{40}$ alkyl or alkenyl group or a $C_1$-$C_{40}$ alkyl phenyl group, more typically a $C_8$-$C_{22}$ alkyl or alkenyl group or a $C_4$-$C_{18}$ alkyl phenyl group, and even more typically a $C_{12}$-$C_{18}$ alkyl group or alkenyl group or a $C_6$-$C_{16}$ alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_9$-$C_{11}$ Pareth-6 Carboxylic Acid, $C_{11}$-$C_{15}$ Pareth-7 Carboxylic Acid, $C_{12}$-$C_{13}$ Pareth-5 Carboxylic Acid, $C_{12}$-$C_{13}$ Pareth-8 Carboxylic Acid, $C_{12}$-$C_{13}$ Pareth-12 Carboxylic Acid, $C_{12}$-$C_{15}$ Pareth-7 Carboxylic Acid, $C_{12}$-$C_{15}$ Pareth-8 Carboxylic Acid, $C_{14}$-$C_{15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In some cases, preferred ethoxylated acids include Oleth-10 Carboxylic Acid, Laureth-5 Carboxylic Acid, Laureth-11 Carboxylic Acid, and a mixture thereof.

(f) Acyl Amino Acids

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of acyl amino acids include those of formula (VIII):

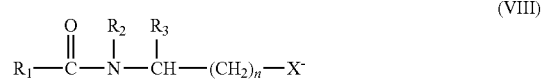

(VIII)

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$.

(g) Acyl Taurates

Non-limiting examples of acyl taurates include those of formula (IX):

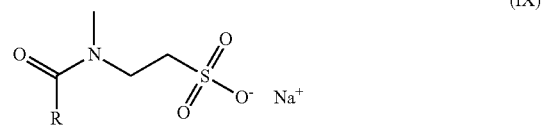

(IX)

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts include sodium cocoyl taurate, sodium methyl cocoyl taurate, sodium lauroyl taurate, and sodium methyl lauroyl taurate.

(h) Acyl Glycinates

Non-limiting examples of acyl glycinates include those of formula (X):

(X)

wherein R is an alkyl chain of 8 to 16 carbon atoms. Although sodium is shown as the cation in the above formula (X), the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

(i) Acyl Glutamates

Non-limiting examples of acyl glutamates include those of formula (XI):

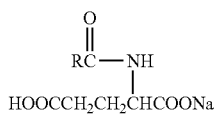

(XI)

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

(j) Acyl Sarcosinates:

Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate.

Fatty Amine Surfactant(s)

The cleansing compositions may include one or more fatty amines typically in an amount of about 0.1 to about 10 wt. %, based on the total weight of the cleansing composition. In some instances, the amount of fatty amine in the cleansing composition is about 0.1 to about 10 wt. %, about 0.2 to about 9 wt. %, about 0.3 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, or about 0.5 to about 2 wt. %; about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, or about 0.5 to about 3 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. % or about 1 to about 3 wt. %; about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %, or about 1.5 to about 2.5 wt. %, including ranges and subranges therebetween, based on the total weight of the cleansing composition.

The cleansing compositions may have at least a portion of the amount of fatty amine that is emulsified and/or not acid neutralized. For example, the cleansing composition may be formulated to have a pH that enables and/or facilitates the fatty amine, or at least a portion thereof, to not be acid neutralized.

The one or more fatty amines may be an amidoamine. Non-limiting examples of suitable amidoamines include, but are not limited to, oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palm itam idopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palm itam idopropyl dimethylamine, stearamidoethyldiethylamine, and a mixture thereof.

The fatty amine may have a structure according to the following formula:

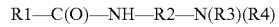

wherein R1 is a fatty acid chain with from 12 to 22 carbon atoms, R2 is an alkylene group containing from one to 4 carbon atoms and R3 and R4 are, independently, an alkyl group having from one to four carbon atoms and from 0.45 to 4% wt. of the composition lactic acid. The fatty amines may be selected from stearamidopropyl dimethylamine, stearamidopropyl diethylamine, stearamidoethyl dimethylamine, stearamidoethyl diethylamine, palimtamidopropyl dimethylamine, behenamidopropyl dimethylamine, myristamidopropyl dimethylamine, oleoamidopropyl dimethylamine, ricinoleoamidopropyl dimethylamine and mixtures.

Nonionic Surfactant(s)

The cleansing compositions include one or more alkoxylated nonionic surfactants in an amount that may vary, but typically ranges from about 0.1 to about 15 wt. %, based on the total weight of the cleansing composition. For instance, the cleansing composition may include nonionic surfactants in an amount ranging from about 0.1 to about 15 wt. %, about 0.1 to about 12 wt. %, about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, or about 0.1 to about 2 wt. %; about 0.5 to about 15 wt. %, about 0.5 to about 12 wt. %, about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, or about 0.5 to about 3 wt. %; about 1 to about 15 wt. %, about 1 to about 12 wt. %, about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, or about 1 to about 2 wt. %; about 2 to about 15 wt. %, about 2 to about 12 wt. %, about 2 to about 10 wt. %, about 2 to about 9 wt. %, about 2 to about 8 wt. %, about 2 to about 7 wt. %, about 2 to about 6 wt. %, about 2 to about 5 wt. %, or about 2 to about 4 wt. %; about 3 to about 15 wt. %, about 3 to about 12 wt. %, about 3 to about 10 wt. %, about 3 to about 9 wt. %, about 3 to about 8 wt. %, about 3 to about 7 wt. %, about 3 to about 6 wt. %, or about 3 to about 5 wt. %; about 4 to about 15 wt. %, about 4 to about 12 wt. %, about 4 to about 10 wt. %, about 4 to about 9 wt. %, about 4 to about 8 wt. %, about 4 to about 7 wt. %, about 4 to about 6 wt. %; about 5 to about 15 wt. %, about 5 to about 12 wt. %, about 5 to about 10 wt. %, about 5 to about 9 wt. %, about 5 to about 8 wt. %, or about 5 to about 7 wt. %, including ranges and subranges therebetween, based on the total weight of the cleansing composition.

The alkoxylated nonionic surfactants may be chosen from alkoxylated alcohols, alkoxylated fatty alcohols, alkoxylated polyol esters such as polyethylene glycol ethers of fatty alcohols, polyethylene glycol ethers of esters, and polyethylene glycol ethers of glycerides, and mixtures thereof. Non-limiting examples of polyethylene glycol ethers of esters include ethoxylated fatty esters. Further discussion of non-limiting examples of the alkoxylated nonionic surfactants are provided below. In some instances, the alkoxylated nonionic surfactants are chosen from PEG-55 propylene glycol oleate, PEG-6 propylene glycol caprylate/caprate, PEG-8 propylene glycol cocoate, PEG-55 propylene glycol oleate, PEG-75 propylene glycol stearate, PEG-25 propylene glycol stearate, PEG-7 glyceryl cocoate, PEG-30 glyceryl cocoate, laureth-2, laureth-3, laureth-4, PEG-200 glyceryl stearate, PEG-120 propylene glycol stearate, PEG-6 Caprylic/Capric Glycerides, and a mixture thereof.

"Alkoxylated nonionic surfactant" as used herein means a compound having at least one alkoxylated portion (—($CH_2$)nO—, where n is an integer from 1 to 300, preferably 2 to 200, or more preferably 2 to 150, even more preferably 2 to 120, or most preferably, 2 to 100).

(a) Alkoxylated Fatty Alcohol

"Alkoxylated fatty alcohol" as used herein means a compound having at least one fatty portion (8 carbon atoms or more) and at least one alkoxylated portion (—(CH2)nO—, where n is an integer of 1 or more). The alkoxylated fatty alcohols of the present invention preferably have an HLB (hydrophilic-lipophilic balance) value from 1-20, including all ranges and subranges therebetween, with HLB values ranging from 1 to 5 (particularly 3 to 5) or from 15-20 (particularly 16 to 18) being preferred. The alkoxylated fatty alcohol may be chosen from ethoxylated fatty alcohols, propoxylated fatty alcohols, and mixtures thereof.

The alkoxylated fatty alcohol can be chosen from di-alkyl, tri-alkyl- and combinations of di-alkyl and tri-alkyl substituted ethoxylated polymers. They can also be chosen from mono-alkyl, di-alkyl, tri-alkyl, tetra-alkyl substituted alkyl ethoxylated polymers and all combinations thereof. The alkyl group can be saturated or unsaturated, branched or linear and contain a number of carbon atoms preferably from about 12 carbon atoms to about 50 carbon atoms, including all ranges and subranges therebetween, for example, 20 to 40 carbon atoms, 22 to 24 carbon atoms, 30 to 50 carbon atoms, and 40 to 60 carbon atoms. Preferably, the fatty portion contains a mixture of compounds of varying carbon atoms such as, for example, $C_{20}$-$C_{40}$ compounds, $C_{22}$-$C_{24}$ compounds, $C_{30}$-$C_{50}$ compounds, and $C_{40}$-$C_{60}$ compounds.

Preferably, the alkoxylated portion of the alkoxylated fatty alcohols of the present disclosure contain 2 or more alkoxylation units, preferably from 2 to 20 alkoxylation units, preferably from 2 to 12 alkoxylation units, preferably from 10 to 200 alkoxylation units, preferably from 20 to 150 alkoxylation units, and preferably from 25 to 100 alkoxylation units, including all ranges and subranges therebetween. Also preferably, the alkoxylation units contain 2 carbon atoms (ethoxylation units) and/or 3 carbon atoms (propoxylation units).

The amount of alkoxylation can also be determined by the percent by weight of the alkoxylated portion with respect to the total weight of the compound. Suitable weight percentages of the alkoxylated portion with respect to the total weight of the compound include, but are not limited to, 10 percent to 95 percent, preferably 20 percent to 90 percent, including all ranges and subranges therebetween with 75 percent to 90 percent (particularly 80 percent to 90 percent) or 20 percent to 50 percent being preferred.

Preferably, the alkoxylated fatty alcohols of the present invention have a number average molecular weight (Mn) greater than 500, preferably from 500 to 5,000, including all ranges and subranges therebetween such as, for example, Mn of 500 to 1250 or an Mn of 2,000 to 5,000.

Suitable examples of alkoxylated fatty alcohols include: laureth-3, laureth-4, laureth-7, laureth-9, laureth-12, laureth-23, ceteth-10, steareth-10, steareth-2, steareth-100, beheneth-5, beheneth-5, beheneth-10, oleth-10, Pareth alcohols, trideceth-10, trideceth-12, C12-13 pareth-3, C12-13 pareth-23, C11-15 pareth-7, PEG hydrogenated castore oil, PEG-75 lanolin, polysorbate-80, polysobate-20, PPG-5 ceteth-20, PEG-55 Propylene Glycol Oleate, glycereth-26 (PEG-26 Glyceryl Ether), PEG 120 methyl glucose dioleate, PEG 120 methyl glucose trioleate, PEG 150 pentaerythrityl tetrastearate, and mixtures thereof.

(b) Alkoxylated Polyol Ester(s)

The alkoxylated polyol esters may be chosen from pegylated derivatives of propylene glycol oleate, propylene glycol caprylate/caprate, propylene glycol cocoate, propylene glycol stearate, and a mixture thereof. In certain embodiments, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In some instances, the polyol ester is or includes PEG-55 propylene glycol oleate. While the alkoxylated polyol esters comprise PEG-200 glyceryl stearate in some embodiments, in other embodiments PEG-200 glyceryl stearate may be excluded. Additionally and/or alternatively, the polyol esters may be chosen from ethoxylated fatty acid esters of sorbitan comprising from 2 to 30 mol of ethylene oxide.

In some cases, the polyol ester may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkylene-oxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Sources of unsaturated polyol esters of glycerol include synthesized oils, natural oils (e.g., vegetable oils, algae oils, bacterial derived oils, and animal fats), combinations of these, and the like. Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, *Carinata* oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, *Perilla* Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, combinations of these, and the like. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The polyol esters may optionally be a natural polyol esters chosen from vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

Additional non-limiting examples of nonionic surfactants that may optionally be used in the cleansing composition include and/or may be chosen from alkanolamides; polyoxyalkylenated nonionic surfactants; polyglycerolated nonionic surfactants; ethoxylated fatty esters; alcohols, alphadiols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

(c) Alkoxylated Glyceride(s)

Non-limiting examples of alkoxylated glycerides that may be suitable in certain embodiments include PEG-6 almond glycerides, PEG-20 almond glycerides, PEG-35 almond glycerides, PEG-60 almond glycerides, PEG-192 apricot kernel glycerides, PEG-11 avocado glycerides, PEG-14 avocado glycerides, PEG-11 babassu glycerides, PEG-42 babassu glycerides, PEG-4 caprylic/capric glycerides, PEG-6 caprylic/capric glycerides, PEG-7 caprylic/capric glycerides, PEG-8 caprylic/capric glycerides, PEG-11 cocoa butter glycerides, PEG-75 cocoa butter glycerides, PEG-7 cocoglycerides, PEG-9 cocoglycerides, PEG-20 corn glycerides, PEG-60 corn glycerides, PEG-20 evening primrose glycerides, PEG-60 evening primrose glycerides, PEG-5 hydrogenated corn glycerides, PEG-8 hydrogenated fish glycerides, PEG-20 hydrogenated palm glycerides, PEG-6 hydrogenated palm/palm kernel glyceride, PEG-16 macadamia glycerides, PEG-70 mango glycerides, PEG-13 mink glycerides, PEG-25 moringa glycerides, PEG-42 mushroom glycerides, PEG-2 olive glycerides, PEG-6 olive glycerides, PEG-7 olive glycerides, PEG-10 olive glycerides, PEG-40 olive glycerides, PEG-18 palm glycerides, PEG-12 palm kernel glycerides, PEG-45 palm kernel glycerides, PEG-60 *Passiflora edulis* seed glycerides, PEG-60 *Passiflora incarnata* seed glycerides, PEG-45 safflower glycerides, PEG-60 shea butter glycerides, PEG-75 shea butter glycerides, PEG-75 shorea butter glycerides, PEG-35 soy glycerides, PEG-75 soy glycerides, PEG-2 sunflower glycerides, PEG-7 sunflower glycerides, PEG-10 sunflower glycerides, PEG-13 sunflower glycerides, PEG-5 tsubakiate glycerides, PEG-10 tsubakiate glycerides, PEG-20 tsubakiate glycerides, PEG-60 tsubakiate glycerides, and sodium PEG-8 palm glycerides carboxylate.

In some embodiments, the at least one alkoxylated nonionic surfactant includes alkoxylated polyol esters such as polyethylene glycol ethers of esters. For example, the polyethylene glycol ethers of esters may be chosen from PEG-55 propylene glycol oleate, PEG-6 propylene glycol caprylate/caprate, PEG-8 propylene glycol cocoate, PEG-25 propylene glycol stearate, PEG-7 glyceryl cocoate, PEG-30 glyceryl cocoate, laureth-2, laureth-3, laureth-4, PEG-200 glyceryl stearate PEG-55 propylene glycol oleate. In further embodiments, the alkoxylated nonionic surfactants comprise a polyethylene glycol ethers of esters and at least one alkoxylated nonionic surfactant other than a polyethylene glycol ether of an ester.

In an embodiment, the at least one alkoxylated nonionic surfactant comprises at least one polyethylene glycol ether of fatty alcohols. For example, the polyethylene glycol ether of fatty alcohol may be chosen from laureth-2, laureth-3, laureth-4, steareth-20, or a mixtures thereof. The polyethylene glycol ether of fatty alcohols may have from 8 to 30 carbon atoms and in particular from 10 to 22 carbon atoms, such as polyethylene glycol ethers of cetyl alcohol, of stearyl alcohol or of cetearyl alcohol (mixture of cetyl alcohol and stearyl alcohol). Mention may be made, for example, of ethers including from 1 to 200 and preferably from 2 to 100 oxyethylene groups, such as those with the CTFA name Ceteareth-20 or Ceteareth-30, and mixtures thereof.

In an embodiment, the at least one alkoxylated nonionic surfactant comprises at least one polyethylene glycol ether of glycerides. For example, the polyethylene glycol ether of glyceride may be chosen from PEG-6 Caprylic/Capric Glycerides). In another embodiment, the cleansing composition comprises at least two alkoxylated nonionic surfactant. Preferably, one of the at least two alkoxylated nonionic surfactants is PEG-55 propylene glycol oleate.

The cleansing composition may optionally include non-alkoxylated nonionic surfactants in an amount that may vary, but typically is in the range of from about 0.1 to about 12 wt. %, about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, or about 0.1 to about 2 wt. %; about 0.5 to about 12 wt. %, about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, or about 0.5 to about 3 wt. %; about 1 to about 12 wt. %, about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, or about 1 to about 2 wt. %; about 2 to about 12 wt. %, about 2 to about 10 wt. %, about 2 to about 9 wt. %, about 2 to about 8 wt. %, about 2 to about 7 wt. %, about 2 to about 6 wt. %, about 2 to about 5 wt. %, or about 2 to about 4 wt. %; about 3 to about 12 wt. %, about 3 to about 10 wt. %, about 3 to about 9 wt. %, about 3 to about 8 wt. %, about 3 to about 7 wt. %, about 3 to about 6 wt. %, or about 3 to about 5 wt. %; about 4 to about 12 wt. %, about 4 to about 10 wt. %, about 4 to about 9 wt. %, about 4 to about 8 wt. %, about 4 to about 7 wt. %, about 4 to about 6 wt. %; about 5 to about 12 wt. %, about 5 to about 10 wt. %, about 5 to about 9 wt. %, about 5 to about 8 wt. %, or about 5 to about 7 wt. %, including ranges and subranges therebetween, based on the total weight of the cleansing composition.

Further nonionic surfactants that may optionally be present in the cleansing composition include:

(d) Glucoside(s)

In some embodiments, the one or more glucosides inlude those chosen from lauryl glucoside, octyl glucoside, decyl glucoside, coco glucoside, caprylyl/capryl glucoside, sodium lauryl glucose carboxylate, and a mixture thereof. Additionally or alternatively, the glucosides may be a alkyl polyglucoside that is chosen from glycerol ($C_6$-$C_{24}$)alkylpolyglycosides including, e.g., polyethoxylated fatty acid mono or diesters of glycerol ($C_6$-$C_{24}$)alkylpolyglycosides. Additional alkyl polyglucosides that may be suitably incorporated, in some instances, in the cleansing composition includes alkyl polyglucosides having a structure according to the following formula:

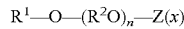

$$R^1-O-(R^2O)_n-Z(x)$$

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Alkyl poly glucosides may, in some instances, include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

(e) Alkanolamide(s)

Non-limiting examples of alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides may include those formed by reacting an alkanolamine and a $C_6$-$C_{36}$ fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof); wherein $R_5$ is selected from —$CH_2OH$, —$CH_2CH_2OH$, —$CH_2CH_2CH_2OH$, —$CH_2(CHOH)_4$ $CH_2OH$, -benzyl, and mixtures thereof; and wherein $R_6$ is selected from —H, —$CH_3$, —$CH_2OH$, —$CH_2CH_3$, —$CH_2CH_2OH$, —$CH_2CH_2CH_2OH$, —$CH_2(CHOH)_4$ $CH_2OH$, -benzyl, and mixtures thereof.

In some instances, the one or more of the fatty acid alkanolamides include one or more acyl glucamides, e.g., acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

(f) Sorbitan Derivative(s)

Suitable sorbitan derivatives that may be incorporated into the plurality of nonionic surfactants include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE(4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearateand a mixture thereof.

Additional and/or alternative sorbitan derivatives include sorbitan esters including, e.g., esters of $C_{16}$-$C_{22}$ fatty acid and of sorbitan that were formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Examples of optional sorbitan esters include sorbitan monostearate (INCI name: Sorbitan stearate) sold by Croda under the name Span 60, the sorbitan tristearate sold by Croda under the name Span 65 V, the sorbitan monopalmitate (INCI name: Sorbitan palmitate) sold by Croda under the name Span 40, the sorbitan monooleate sold by Croda under the name Span 80 V or the sorbitan trioleate sold by Uniqema under the name Span 85 V. A preferable sorbitan ester is sorbitan tristearate.

Polyol(s)

The cleansing compositions may include one or more polyols typically in an amount of about 1 to about 10 wt. %, based on the total weight of the cleansing composition. In some instances, the amount of polyols in the cleansing composition is about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, or about 1 to about 2 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %, or about 2 to about 3 wt. %; about 3 to about 10 wt. %, about 3 to about 9 wt. %, about 3 to about 8 wt. %, about 3 to about 7 wt. %, about 3 to about 6 wt. %, about 3 to about 5 wt. %, or about 3 to about 4 wt. %; about 4 to about 10 wt. %, about 4 to about 9 wt. %, about 4 to about 8 wt. %, about 4 to about 7 wt. %, about 4 to about 6 wt. %, or about 4 to about 5 wt. %, including ranges and subranges therebetween, based on the total weight of the cleansing composition.

The term "polyol" should be understood as meaning, within the meaning of the present disclosure, an organic molecule comprising at least two free hydroxyl groups. The polyols of the cleansing composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the cleansing composition, in certain instances, include ethylene glycol, propylene glycol, butylene glycol, hexylene glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the cleansing composition comprises at least propylene glycol, and optionally one or more polyols other than propylene glycol.

Non-limiting examples of polyols that may, optionally, be included in the hair care include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, and a mixture thereof.

Thickening Agent(s)

The cleansing compositions described herein may, optionally, include a thickening agent. The amount of thickening agents can vary but is typically from about 0.01 to about 20 wt. %, based on the total weight of the cleansing composition. In some instances, the amount of fatty compounds present in the cleansing compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the cleansing composition.

The thickening agent(s) may be chosen from xanthan gum, guar gum, biosaccharide gum, cellulose, acacia seneca gum, *sclerotium* gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate. Suitable thickening agents may be found in U.S. patent application Ser. No. 16/731,654, which is incorporated herein, in its entirety for all purposes.

Many thickening agents are water-soluble, and increase the viscosity of water or form an aqueous gel when the cleansing composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the cleansing compositions of the instant disclosure. Thickening agents may be referred to as "thickeners" or "viscosity modifying agents." Thickening agents are typically included to increase the viscosity of the cleansing compositions. Nonetheless, in some instances, certain thickening agents provide additional, surprising benefits to the cleansing compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters:

Non-limiting polyglycerol esters of fatty acids (polygylceryl esters) include those of the following formula:

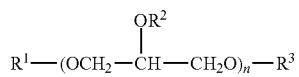

$$R^1-(OCH_2-CH(OR^2)-CH_2O)_n-R^3$$

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, Seneca gum, *sclerotium* gum, gellan gum, etc.

pH Adjuster(s)

The cleansing composition may include one or more pH adjusters to increase or decrease the overall pH of the cleansing composition. For example, one or more acids may be included to decrease the pH of the cleansing composition. Examples of suitable acids for decreasing the pH of the cleansing composition include, but are not limited to, citric acid, acetic acid, and the like. The cleansing composition may include one or more bases, such as sodium hydroxide, potassium hydroxide and the like, to increase the pH of the cleansing composition. Additional or alternative acids and bases that are suitable for adjusting the pH of the cleansing composition are readily known to one of ordinary skill in the art.

The cleansing compositions typically have a pH of about 3 to about 7.5. Preferably, the cleansing compositions have a pH of about 4 to about 7, about 4.5 to about 7, about 5 to about 7, about 5.5 to about 7, or about 6 to about 7; about 4 to about 6.5, about 4.5 to about 6.5, about 5 to about 6.5, or about 5.5 to about 6.5; about 4 to about 6, about 4.5 to about 6, or about 5 to about 6; or about 4 to about 5, or about 4.5 to about 5, including ranges and subranges therebetween.

The amount of the pH adjuster in the cleansing composition may be based on the desired pH of the final cleansing composition and/or product. For example, the total amount of the pH adjuster may range from about 0.05 to about 20 wt. %, based on the total weight of the cleansing composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the cleansing composition.

Chelating Agent(s)

The cleansing composition may, optionally, include chelating agents. The amount of chelating agent present in the cleansing composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the cleansing composition.

Non-limiting examples of chemical chelating agents include aminotrimethyl phosphonic acid, ß-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and YNa$_4$), potassium (YH$_3$K, Y$_2$H$_3$K$_3$ and YK$_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate.

In some embodiments, the chelating agents are selected from sodium phytate, ethylenediaminetetraacetic acid (EDTA), tetrasodium etidronate, tetrasodium pyrophosphate, pentasodium ethylenediamine tetramethylene phosphonate, sodium staminate and combinations of these.

Preservative(s)

Preservatives may be included in the cleansing composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the cleansing composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Water

The cleansing compositions may include water in an amount of about 50 to 92.9 wt. %. For example, the cleansing compositions may have water present in an amount of about 50 to 92.9 wt. %, about 60 to 92.9 wt. %, about 65 to 92.9 wt. %, about 70 to 92.9 wt. %, about 70 to 92.9 wt. %, about 75 to 92.9 wt. %, about 80 to 92.9 wt. %, about 85 to 92.9 wt. %; about 50 to about 85 wt. %, about 60 to about 85 wt. %, about 65 to about 85 wt. %, about 70 to about 85 wt. %, about 70 to about 85 wt. %, about 75 to about 85 wt. %, about 80 to about 85 wt. %; about 50 to about 80 wt. %, about 60 to about 80 wt. %, about 65 to about 80 wt. %, about 80 wt. %, about 70 to about 80 wt. %, about 70 to about 80 wt. %, about 75 to about 80 wt. %, including any ranges or subranges therebetween, based on the total weight of the cleansing composition.

Methods of Cleansing Hair

Methods of cleansing hair according to the disclosure may vary but typically include applying a cleansing composition as disclosed herein, allowing the cleansing composition to remain on the hair for a sufficient amount of time, and rinsing the cleansing compositions from the hair. The cleansing composition may be applied to the hair in a sequence with other compositions. For example, the cleansing composition may be applied to the hair before conditioning the hair and/or after conditioning the hair. The cleansing compositions, however, are not required to be used in a sequence.

The methods may include applying an amount of the cleansing composition onto the user's hair, for example, onto one or both hands, onto the hair, etc. The user's hair may already be wet or damp with extraneous water or extraneous water can be included after the cleansing composition has already been applied to the hair. The extraneous water typically has a temperature of about 25° to 50° C. The cleansing composition may be applied to the user's hand(s) or directly to the hair while the user is showering and/or bathing in water having a temperature of, e.g., 25° to 50° C. The cleansing composition may optionally be rinsed from the user's hair.

EMBODIMENTS OF THE DISCLOSURE

In certain embodiments of the present disclosure, the cleansing compositions is a shampoo composition comprising:

about 6 wt. % or more, preferably about 6 to about 25 wt. %, more preferably about 6 to about 16 wt. %, of one or more betaine surfactants, such as cocamidopropyl betaine, coco-betaine, or a mixture thereof;

about 5 wt. % or less, preferably about 4.75 wt. % or less, more preferably about 4.5 wt. % or less, even more preferably about 4 wt. % or less of one or more anionic surfactants, e.g., where the one or more anionic surfactants are chosen from amino acid surfactants, isethionate surfactants, or a mixture thereof;

about 0.1 wt. % to about 10 wt. %, preferably about 0.2 to about 9 wt. %, more preferably about 0.5 to about 7 wt. %, of one or more fatty amine surfactants, preferably one or more fatty amine surfactants chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palm itamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, m inkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palm itam idopropyl dimethylamine, stearamidoethyldiethylamine, and a mixture thereof;

about 0.1 to about 15 wt. %, preferably about 0.1 to about 10 wt. %, more preferably about 1 to about 10 wt. %, of one or more nonionic surfactants, wherein at least one of the one or more nonionic surfactants is chosen from alkoxylated nonionic surfactants, such as alkoxylated fatty alcohols, polyethylene glycol ethers of fatty alcohols, or a mixture thereof;

wherein the shampoo composition has a weight ratio of the total amount of (a) to the total amount of (b)+(c)+(d) of 0.8:1 to 5:1, preferably 0.85:1 to 5:1, more preferably 0.85:1 to 4:1; and water, preferably in an amount of about 50 to 92.9 wt. %, more preferably about 65 to about 85 wt. %, wherein the shampoo composition is substantially free of anionic sulfate surfactants and substantially free of silicones, and wherein all weight percentages are based on the total weight of the shampoo composition.

In further embodiments of the present disclosure, provided is a shampoo composition comprising:

about 6 to about 20 wt. %, preferably about 6 to about 16 wt. %, more preferably about 6 to about 12 wt. %, of two or more betaine surfactants, such as cocamidopropyl betaine, coco-betaine, or a mixture thereof;

about 0.2 to about 3 wt. %, preferably about 0.2 to about 2.5 wt. %, more preferably about 0.2 to about 2 wt. %, of one or more non-sulfate anionic surfactants chosen from sodium methyl cocoyl taurate, sodium lauroyl methyl isethionate, or a mixture thereof;

about 0.1 wt. % to about 10 wt. %, preferably about 0.2 to about 9 wt. %, more preferably about 0.5 to about 7 wt. %, of stearamidopropyl dimethylamine;

about 0.1 to about 10 wt. %, preferably about 1 to about 10 wt. %, more preferably about 1 to about 9 wt. %, of PEG-55 propylene glycol oleate;

wherein the shampoo composition has a weight ratio of the total amount of (a) to the total amount of (b)+(c)+(d) of 0.8:1 to 5:1, preferably 0.85:1 to 5:1, more preferably 0.85:1 to 4:1, water, preferably in an amount of about 50 to 92.9 wt. %, more preferably about 65 to about 85 wt. %; and about 0.1 to about 10 wt. %, preferably about 1 to about 10 wt. %, more preferably about 1 to about 9 wt. %, of a one or more polyols, such as those chosen from ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, glycerin, diglycerin, caprylyl glycol, and a mixture thereof, wherein the shampoo composition is substantially free of anionic sulfate surfactants and substantially free from silicones, and wherein all weight percentages are based on the total weight of the shampoo composition.

In other embodiments of the present disclosure, provided is a method for cleansing hair comprising applying a shampoo composition to the hair, and rinsing the shampoo composition from the hair, wherein the shampoo composition comprises:

about 6 wt. % or more, preferably about 6 to about 25 wt. %, more preferably about 6 to about 16 wt. %, of one or more betaine surfactants, such as cocamidopropyl betaine, coco-betaine, or a mixture thereof;

about 5 wt. % or less, preferably about 4.75 wt. % or less, more preferably about 4.5 wt. % or less, even more preferably about 4 wt. % or less of one or more anionic surfactants, e.g., where the one or more anionic surfactants are chosen from amino acid surfactants, isethionate surfactants, or a mixture thereof;

about 0.1 wt. % to about 10 wt. %, preferably about 0.2 to about 9 wt. %, more preferably about 0.5 to about 7 wt. %, of one or more fatty amine surfactants, preferably one or more fatty amine surfactants chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palm itamidopropyl dimethylamine, ricinoleamidopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palm itam idopropyl dimethylamine, stearamidoethyldiethylamine, and a mixture thereof;

about 0.1 to about 15 wt. %, preferably about 0.1 to about 10 wt. %, more preferably about 1 to about 10 wt. %, of one or more nonionic surfactants, wherein at least one of the one or more nonionic surfactants is chosen from alkoxylated nonionic surfactants, such as alkoxylated fatty alcohols, polyethylene glycol ethers of fatty alcohols, or a mixture thereof, wherein the one or more nonionic surfactant preferably comprises PEG-55 propylene glycol oleate and optionally another alkoxylated nonionic surfactants;

wherein the shampoo composition has a weight ratio of the total amount of (a) to the total amount of (b)+(c)+(d) of 0.8:1 to 5:1, preferably 0.85:1 to 5:1, more preferably 0.85:1 to 4:1; and water, preferably in an amount of about 50 to 92.9 wt. %, more preferably about 65 to about 85 wt. %, wherein the shampoo composition is substantially free of anionic sulfate surfactants and substantially free of silicones, and wherein all weight percentages are based on the total weight of the shampoo composition.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Implementation of the present disclosure is provided by way of the following examples. The following examples serve to elucidate aspects of the technology without being limiting in nature.

Example 1

Exemplary Compositions

Five non-limiting example compositions (Examples A-E) were prepared based on the formulations provided in Table 1, below.

TABLE 1

|  |  | US INCI Name | A | B | C | D | E |
|---|---|---|---|---|---|---|---|
| (a) | Betaine surfactants | COCAMIDOPROPYL BETAINE | 6.1 | 8.4 | 6.5 | 7.8 | 8.6 |
|  |  | COCO-BETAINE | 2.7 | 3.3 | 1.8 | 2.6 | 2.6 |
|  |  | Total Betaine Surfactants | 8.8 | 11.7 | 8.3 | 10.4 | 11.2 |
| (b) | Non-Sulfate Anionic Surfactants | SODIUM METHYL COCOYL TAURATE | 0.7 | 2.2 |  | 2.2 | 2.2 |
|  |  | SODIUM LAUROYL METHYL ISETHIONATE |  |  | 1 |  |  |
| (c) | Fatty Amine Surfactant | STEARAMIDOPROPYL DIMETHYLAMINE | 2.5 | 2.5 | 2.5 | 1.5 | 1.5 |

TABLE 1-continued

| | US INCI Name | A | B | C | D | E |
|---|---|---|---|---|---|---|
| (d) Nonionic Surfactants | PEG-55 PROPYLENE GLYCOL OLEATE | 1.6 | 0.4 | 0.8 | 0.2 | 0.2 |
| | DECYL GLUCOSIDE AND/OR CAPRYLYL/CAPRYL GLUCOSIDE | 3 | | | | 3 |
| | Total Amount of (a) + (b) | 9.5 | 13.9 | 9.3 | 12.6 | 13.4 |
| | Ratio of (a):(b) | 12.6:1 | 5.3:1 | 8.3:1 | 4.7:1 | 5.1:1 |
| | Total Amount of (b) + (c) + (d) | 7.8 | 5.1 | 4.3 | 3.9 | 6.9 |
| | Ratio of (a):((b) + (c) + (d)) | 1.1:1 | 2.3:1 | 1.9:1 | 2.7:1 | 1.6:1 |
| (f) Polyol | PROPYLENE GLYCOL | 1.6 | 0.4 | 0.8 | 0.2 | 0.2 |
| Salt | SODIUM CHLORIDE | 1.7 | 2.3 | 1.6 | 2.0 | 2.1 |
| Miscellaneous (e.g., active ingredients, pH adjusters, preservatives, chelating agent, etc. | SALICYLIC ACID, CITRIC ACID, SODIUM BENZOATE, TRISODIUM ETHYLENEDIAMINE DISUCCINATE, | ≤2.0 | ≤2.0 | ≤2.0 | ≤2.0 | ≤2.0 |
| (e) Water | WATER | QS to 100 | QS to 100 | QS to 100 | QS to 100 | QS to 100 |
| Viscosity at a temperature of 24° C. as measured with RV-4 Disk spindle on a Brookfield DV2T viscometer at a range of 5-20 rpm after 90 seconds | | 4000 cPs | 7000 cPs | 7600 cPs | 3000 cPs | 6000 cPs |

Example 2

Evaluation of Example Composition A

Example Composition A was evaluated in comparison to Benchmark Composition 1. The formulation for Benchmark Composition 1 is provided below.

TABLE 2

| | INCI US name | Benchmark Composition 1 (Wt. %) |
|---|---|---|
| Amphoteric surfactant | COCAMIDOPROPYL BETAINE | 1.5 |
| Anionic surfactant | SODIUM LAURETH SULFATE, and/or SODIUM SARCOSINATE | 14 |
| Nonionic surfactant | TRIDECETH-3, TRIDECETH-10, STEARETH-6, and PEG-100 STEARATE | 0.3 |
| | Ratio of betaine surfactants to total amount of anionic surfactants, fatty amine surfactants, and nonionic surfactants | 1:9.6 |
| Polyol | GLYCERIN, PROPYLENE GLYCOL, HEXYLENE GLYCOL, PEG-45M, and GLYCOL DISTEARATE | 0.5-1.0 |
| Silicones | DIMETHICONE, AMODIMETHICONE, and POTASSIUM DIMETHICONE PEG-7 PANTHENYL PHOSPHATE | 1.5-2.0 |
| Cationic Polymer | GUAR HYDROXYPROPYLTRIMONIUM CHLORIDE | 0.1-0.3 |
| Thickening agent | CARBOMER | 0.2-0.5 |
| Preservatives | SODIUM BENZOATE, PHENOXYETHANOL, BHT, POTASSIUM SORBATE, and TETRASODIUM EDTA | ~0.5 |
| Pigments and/or Color Agents | MICA, TITANIUM DIOXIDE, and CARAMEL | 0.3≥ |
| Miscellaneous Ingredients (Active Ingredients, salts, fragrance, etc.) | GLUCOSE, HYDROLYZED SOY PROTEIN, SALICYLIC ACID, FUMARIC ACID, ARGININE, HYDROLYZED VEGETABLE PROTEIN PG-PROPYL SILANETRIOL, PLUKENETIA VOLUBILIS SEED OIL, ALOE BARBADENSIS LEAF JUICE POWDER, SODIUM COCOYL AMINO ACIDS, *CEREUS GRANDIFLORUS* (CACTUS) FLOWER EXTRACT, ACETIC ACID, LACTIC ACID, CITRIC ACID, SODIUM CHLORIDE, and FRAGRANCE | 5.0≥ |
| Water | WATER | Q.S. 100 |

Six volunteers having medium to long hair with hair curl patterns of 1-3 and sensitivity of 1-3 each received 10 grams (g) of Example Composition A and Benchmark Composition 1. Specifically, Example Composition A was applied to a first half of each volunteer's head of hair while Benchmark Composition 1 was applied to the other half of each volunteer's head of hair.

The compositions were massaged onto the hair and evaluated. Benchmark Composition 1 produced more foam and had better foam properties than Example Composition A during application of the compositions. However, Example Composition A exhibited a better smoothness in foam, ease of passing fingers, and suppleness while rinsing the compositions from the hair.

The hair of the volunteers was also evaluated after the compositions were rinsed from the hair. While the hair was still wet, the hair washed with Example Composition A exhibited noticeably better smoothness and suppleness in comparison to Benchmark Composition 1.

The hair was subsequently blow-dried and no conditioner was applied to the hair. After blow drying the hair, the hair receiving Example Composition A exhibited noticeable better ease of shaping, tactile and visual smoothness, hair discipline and more weight than Benchmark Composition 1. Benchmark Composition 1 exhibited noticeably better dry ends than Example Composition 1.

Overall, the hair receiving Example Composition A exhibited better smoothness, suppleness, sealed ends, ease of blow drying, ease of combining, and shine. Additionally, Example Composition A provided slightly more volume and root lift (which is associated with cleansing of the hair). Although Example Composition A provided more coating and weight to the hair, the amount of coating and weight provided by Example Composition A was suitable and still acceptable. Moreover, while Benchmark Composition 1, produced more foam than Example Composition A, the foam quality and volume for Example Composition A was still acceptable.

Example 3

Compositions Having Additional PEGylated Surfactant and Sebum

Five exemplary compositions (Example Compositions F-J) were prepared having a formulation similar to Example Composition A, except that the five compositions included an additional PEGylated surfactant. Six additional compositions (Compositions AS and FS-JS) were prepared by adding sebum to Example Compositions A and F-J. Compositions AS and FS-JS are representative of the application of Example Compositions A and F-J to a user's hair, which has sebum, for the purpose of evaluating viscosity and foaming properties. The formulations for Example Compositions A and F-J and Compositions AS and FS-JS are shown on the follow pages in Table 3.

Example Compositions A and F-J and Compositions AS and FS-JS were evaluated to assess their respective viscosities using a Brooksfield viscometer/rheometer using a RV-4 Disk spindle at a speed of 5-20 rpm. FIG. 1 provides a graph showing the viscosity of Example Compositions A and F-J and Compositions AS and FS-JS.

Figure 2:
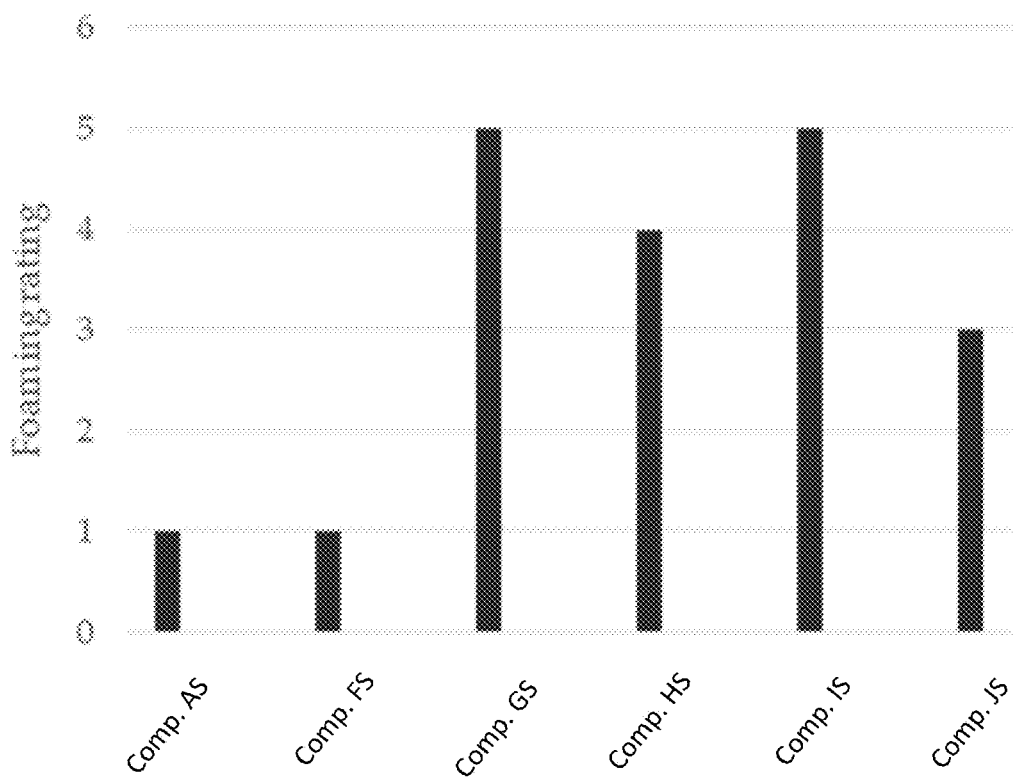
FIG. 2 is a bar graph showing the effect of PEGylated surfactants and sebum on the foaming rating of cleansing compositions according to an aspect of the disclosure.

Compositions AS and FS-JS were evaluated to determine their foam rating. Specifically, a mannequin head was first rinsed with warm water, then 5.0 gram of respective samples of Compositions AS and FS-JS were applied onto half of the head of hair of the mannequin and 5.0 gram of the Benchmark Composition 1 on the other half of head of hair. The samples of Compositions AS and FS-JS and Benchmark Composition 1 was lathered up and the foam was rated with an assigned value of 1 to 5 (5 is the most abundant of foam). A graph showing the foam rating of Compositions AS and FS-JS is provided in FIG. 2.

TABLE 3

| | | US INCI Name | A (wt. %) | AS (wt. %) | F (wt. %) | FS (wt. %) | G (wt. %) | GS (wt. %) |
|---|---|---|---|---|---|---|---|---|
| (a) | Betaine surfactants | COCAMIDOPROPYL BETAINE | 6.1 | 5.9 | 6.0 | 5.7 | 6.0 | 5.7 |
| | | COCO-BETAINE | 2.7 | 2.6 | 2.7 | 2.5 | 2.6 | 2.5 |
| | | Total Betaine Surfactants | 8.8 | 8.5 | 8.6 | 8.3 | 8.6 | 8.3 |
| (b) | Non-Sulfate Anionic Surfactants | SODIUM METHYL COCOYL TAURATE | 0.7 | 0.7 | 0.7 | 0.7 | 0.7 | 0.7 |
| (c) | Fatty Amine Surfactant | STEARAMIDOPROPYL DIMETHYLAMINE | 2.5 | 2.4 | 2.5 | 2.4 | 2.5 | 2.4 |
| (d) | Nonionic surfactants | PEG-55 PROPYLENE GLYCOL OLEATE | 1.6 | 1.5 | 1.6 | 1.5 | 1.6 | 1.5 |
| | | CAPRYLYL/CAPRYL GLUCOSIDE | 3 | 2.9 | 2.9 | 2.8 | 2.9 | 2.8 |
| | | LAURETH-2 AND LAURETH-3 | | | 2.0 | 1.9 | | |
| | | PEG-6 CAPRYLIC/CAPRIC GLYCERIDES | | | | | 2.0 | 1.9 |
| | | PEG-7 GLYCERYL COCOATE | | | | | | |
| | | PEG-30 GLYCERYL COCOATE | | | | | | |
| | | PEG-200 GLYCERYL STEARATE | | | | | | |
| | | Total Amount of (a) + (b) | 9.5 | 9.2 | 9.3 | 9 | 9.3 | 9 |
| | | Ratio of (a):(b) | 12.6:1 | 12.1:1 | 12.3:1 | 11.9:1 | 12.3:1 | 11.9:1 |
| | | Total Amount of (b) + (c) + (d) | 7.8 | 7.5 | 9.6 | 9.2 | 9.6 | 9.2 |
| | | Ratio of (a):((b) + (c) + (d)) | 1:0.89 | 1:0.88 | 1:1.1 | 1:1.1 | 1:1.1 | 1:1.1 |
| (f) | Polyol | PROPYLENE GLYCOL | 4.4 | 1.5 | 1.6 | 1.5 | 1.6 | 1.5 |
| | Salt | SODIUM CHLORIDE | 1.7 | 1.6 | 1.7 | 1.6 | 1.7 | 1.6 |
| | Miscellaneous (e.g., active ingredients, pH adjusters, preservatives, chelating agent, etc.) | | ≤2.0 | ≤2.0 | ≤2.0 | ≤2.0 | ≤2.0 | ≤2.0 |
| | | Sebum | | 3.8 | | 3.8 | | 3.8 |
| (e) | Water | WATER | QS | QS | QS | QS | QS | QS |

| | | US INCI Name | H (wt. %) | HS (wt. %) | I (wt. %) | IS (wt. %) | J (wt. %) | JS (wt. %) |
|---|---|---|---|---|---|---|---|---|
| (a) | Betaine surfactants | COCAMIDOPROPYL BETAINE | 6.0 | 5.7 | 6.0 | 5.7 | 6.0 | 5.7 |
| | | COCO-BETAINE | 2.7 | 2.5 | 2.7 | 2.5 | 2.7 | 2.5 |
| | | Total Betaine Surfactants | 8.6 | 8.3 | 8.6 | 8.3 | 8.6 | 8.3 |
| (b) | Non-Sulfate Anionic Surfactants | SODIUM METHYL COCOYL TAURATE | 0.7 | 0.7 | 0.7 | 0.7 | 0.7 | 0.7 |
| (c) | Fatty Amine Surfactant | STEARAMIDOPROPYL DIMETHYLAMINE | 2.5 | 2.4 | 25 | 2.4 | 2.5 | 2.4 |

TABLE 3-continued

| | | | | | | | |
|---|---|---|---|---|---|---|---|
| (d) Nonionic surfactants | PEG-55 PROPYLENE GLYCOL OLEATE | 1.6 | 1.5 | 1.6 | 1.5 | 1.6 | 1.5 |
| | CAPRYLYL/CAPRYL GLUCOSIDE | 2.9 | 2.2 | 2.9 | 2.8 | 2.9 | 2.8 |
| | LAURETH-2 AND LAURETH-3 | | | | | | |
| | PEG-6 CAPRYLIC/CAPRIC GLYCERIDES | | | | | | |
| | PEG-7 GLYCERYL COCOATE | 2.0 | 1.9 | | | | |
| | PEG-30 GLYCERYL COCOATE | | | 2.0 | 1.9 | | |
| | PEG-200 GLYCERYL STEARATE | | | | | 2.0 | 1.9 |
| | Total Amount of (a) + (b) | 9.3 | 9 | 9.3 | 9 | 9.3 | 9 |
| | Ratio of (a):(b) | 12.3:1 | 11.9:1 | 12.3:1 | 11.9:1 | 12.3:1 | 11.9:1 |
| | Total Amount of (b) + (c) + (d) | 9.6 | 9.2 | 9.6 | 9.2 | 9.6 | 9.2 |
| | Ratio of (a):((b) + (c) + (d)) | 1:1.1 | 1:1.1 | 1:1.1 | 1:1.1 | 1:1.1 | 1:1.1 |
| (f) Polyol | PROPYLENE GLYCOL | 1.6 | 1.5 | 1.6 | 1.5 | 1.6 | 1.5 |
| Salt | SODIUM CHLORIDE | 1.7 | 1.6 | 1.7 | 1.6 | 1.7 | 1.6 |
| Miscellaneous (e.g., active ingredients, pH adjusters, preservatives, chelating agent, etc.) | | ≤2.0 | ≤2.0 | ≤2.0 | ≤2.0 | ≤2.0 | ≤2.0 |
| | Sebum | | 3.8 | | 3.8 | | 3.8 |
| (e) Water | WATER | QS | QS | QS | QS | QS | QS |

Viscosity and foaming measurements on the compositions in Table 3 were conducted. In general, viscosity may have an impact on the homogeneous distribution, spreadability, and ease of application of cleansing compositions, such as a shampoo, onto hair. For example, lower viscosities lead to improved distribution, spreadability, and ease of application onto hair. At the same time, higher foaming ratings, which typically correlate to higher viscosities, are desirable for a shampoo.

The viscosity and foaming measurements show that the additional presence of PEG-6 caprylic/capric glycerides, PEG-7 glyceryl cocoate, and/or PEG-30 glyceryl cocoate (see Example Compositions G, H, and I) resulted in lower viscosities and higher foaming ratings as compared to the ratings for Example Composition A. Even when sebum was present, e.g., as in Example Compositions GS, HS, and IS, the viscosities of the compositions did not increase as much as compared to the viscosity of Example Composition AS (with sebum). At the same time, the foaming ratings for Example Compositions GS, HS, and IS were much higher than the foaming rating for Example composition AS.

As for the presence of laureth-2 and laureth-3 in Example Composition F, the viscosity of this composition increased as compared to the viscosity of Example Composition A. However, even in the presence of sebum, the viscosity of Example composition FS did not change significantly.

As for the presence of PEG-200 glyceryl stearate, Example Composition J had a higher viscosity than that of Example composition A and when sebum was added (See Composition JS), the viscosity increased significantly compared to the viscosity of Example composition J. The viscosity of Composition JS was also significantly higher than the viscosities of all the other compositions (with or without sebum). At the same time, the foaming rating of Composition JS was higher than that of Compositions AS and FS, but it was not as high as that of Compositions GS, HS, and IS.

The invention claimed is:
1. A shampoo composition comprising:
   (a) at least 6 wt. % of one or more betaine surfactants;
   (b) about 5 wt. % or less of one or more non-sulfate anionic surfactants;
   (c) about 0.1 wt. % to about 10 wt. % of one or more fatty amine surfactants;
   (d) about 0.1 to 8 wt. % of one or more nonionic surfactants, wherein at least one of the one or more nonionic surfactants is an alkoxylated nonionic surfactant;
   wherein the shampoo composition has a weight ratio of (a) to ((b)+(c)+(d)) of 0.8:1 to 5:1, and
   (a) is in an amount greater than (d); and
   (e) water;
   wherein the shampoo composition is substantially free of anionic sulfate surfactants,
   the shampoo composition is substantially free of silicones, and
   all weight percentages are based on the total weight of the shampoo composition.
2. The shampoo composition of claim 1, wherein the one or more betaine surfactants are chosen from cocamidopropyl betaine and coco-betaine.
3. The shampoo composition of claim 1 comprising at least 6 to about 20 wt. % of two or more betaine surfactants.
4. The shampoo composition of claim 3 comprising cocamidopropyl betaine and coco-betaine.
5. The shampoo composition of claim 1, wherein the one or more non-sulfate anionic surfactants are chosen from amino acid surfactants and isethionate surfactants.
6. The shampoo composition of claim 1, wherein at least one of the one or more non-sulfate anionic surfactants is an amino acid surfactant.
7. The shampoo composition of claim 1, wherein at least one of the one or more non-sulfate anionic surfactants is a taurate surfactant.
8. The shampoo composition of claim 1, wherein at least one of the one or more non-sulfate anionic surfactants is an isethionate surfactant.
9. The shampoo composition of claim 1, wherein at least a portion of the fatty amine is emulsified and not acid neutralized.

10. The shampoo composition of claim 1, wherein at least one of the one or more fatty amines is an amidoamine chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, and stearamidoethyldiethylamine.

11. The shampoo composition of claim 1, wherein the alkoxylated nonionic surfactant is chosen from polyethylene glycol ether of esters, polyethylene glycol ether of fatty alcohols, polyethylene glycol ether of glycerides, or a mixture thereof.

12. The shampoo composition of claim 1, wherein the alkoxylated nonionic surfactant is chosen from PEG-55 propylene glycol oleate, PEG-6 propylene glycol caprylate/caprate, PEG-8 propylene glycol cocoate, PEG-25 propylene glycol stearate, PEG-7 glyceryl cocoate, PEG-30 glyceryl cocoate, laureth-2, laureth-3, laureth-4, PEG-120 propylene glycol stearate, PEG-6 caprylic/capric glycerides, or a mixture thereof.

13. The shampoo composition of claim 1, wherein the one or more nonionic surfactants further comprise a glucoside.

14. The shampoo composition of claim 1 further comprising:
(f) about 0.1 to about 10 wt. % of one or more polyols chosen from ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, glycerin, diglycerin, and caprylyl glycol.

15. The shampoo composition of claim 1, wherein about 90% or more, by weight, of all compounds are biodegradable according to OECD Test Guidelines No. 301 A, B, C, D, E, and/or F.

16. The shampoo composition of claim 1 comprising 2.5 wt. % or less of the one or more non-sulfate anionic surfactants.

17. The shampoo composition of claim 1, wherein (a) is in an amount greater than ((b)+(c)+(d)).

18. A shampoo composition comprising:
(a) at least 6 to about 20 wt. % of two or more betaine surfactants;
(b) about 0.2 to about 3 wt. % of one or more non-sulfate anionic surfactants chosen from sodium methyl cocoyl taurate, sodium cocoyl taurate, sodium lauroyl methyl isethionate, sodium isethionate, sodium cocoyl isethionate, and sodium cocoyl methyl isethionate;
(c) about 0.1 wt. % to about 10 wt. % of stearamidopropyl dimethylamine;
(d) about 0.1 to about 10 wt. % of PEG-55 propylene glycol oleate;
wherein the shampoo composition has a weight ratio of (a) to ((b)+(c)+(d)) of 0.8:1 to 5:1, and
(a) is in an amount greater than (d);
(e) water; and
(f) about 0.1 to about 10 wt. % of a one or more polyols,
wherein the shampoo composition is transparent,
the shampoo composition is substantially free of anionic sulfate surfactants and substantially free from silicones, and
all weight percentages are based on a total weight of the shampoo composition.

19. A shampoo composition consisting of:
(a) at least 6 to about 20 wt. % of two or more betaine surfactants;
(b) about 0.3 to about 3 wt. % of one or more non-sulfate anionic surfactants chosen from amino acid surfactants and isethionate surfactants;
(c) about 0.1 wt. % to about 10 wt. % of one or more amidoamine surfactants;
(d) about 0.1 to about 10 wt. % of one or more nonionic surfactants, wherein at least one of the one or more nonionic surfactants is an alkoxylated nonionic surfactant;
wherein the shampoo composition has a weight ratio of (a) to ((b)+(c)+(d)) of 0.8:1 to 5:1, and
(a) is in an amount greater than (d); and
(e) water;
(f) about 0.1 to about 10 wt. % of one or more polyols;
(g) optionally, one or more pH adjusters;
(h) optionally, one or more preservatives;
(i) optionally, one or more chelating agents;
(j) optionally, one or more colorants; and
(k) optionally, up to 5 wt. % of one or more miscellaneous components;
wherein all weight percentages are based on a total weight of the cleansing composition.

20. A method for cleansing hair comprising applying a shampoo composition of claim 1 to the hair, and rinsing the shampoo composition from the hair.

\* \* \* \* \*